(12) United States Patent
Boehm et al.

(10) Patent No.: US 10,117,726 B2
(45) Date of Patent: Nov. 6, 2018

(54) PLUNGER ASSEMBLY AND A CAPSULE FOR DISPENSING A DENTAL MATERIAL

(71) Applicant: 3M INNOVATIVE PROPERTIES COMPANY, St. Paul, MN (US)

(72) Inventors: Andreas J. Boehm, Reichling (DE); Marc Peuker, Schöndorf (DE); Arno Hohmann, München (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 14/779,781

(22) PCT Filed: Mar. 21, 2014

(86) PCT No.: PCT/US2014/031391
§ 371 (c)(1),
(2) Date: Sep. 24, 2015

(87) PCT Pub. No.: WO2014/160593
PCT Pub. Date: Oct. 2, 2014

(65) Prior Publication Data
US 2016/0045283 A1 Feb. 18, 2016

(30) Foreign Application Priority Data
Mar. 26, 2013 (EP) .................................. 13160991

(51) Int. Cl.
*A61C 5/62* (2017.01)
*A61C 5/64* (2017.01)
(Continued)

(52) U.S. Cl.
CPC .................. *A61C 5/62* (2017.02); *A61C 5/64* (2017.02); *A61C 5/66* (2017.02); *A61C 5/68* (2017.02)

(58) Field of Classification Search
CPC ......... A61C 5/064; A61C 5/062; A61C 5/066; A61C 5/068; A61C 5/62; A61C 5/64; A61C 5/66; A61C 5/68
See application file for complete search history.

(56) References Cited

U.S. PATENT DOCUMENTS 2,754,590 A * 7/1956 Cohen ...................... A61C 5/04
433/90
3,370,754 A * 2/1968 Schumann ............. A61C 5/064
222/132
(Continued)

FOREIGN PATENT DOCUMENTS

| CA | 2699127 | 10/2010 |
| JP | 6-296038 | 10/1994 |

(Continued)

OTHER PUBLICATIONS

International Search Report for PCT International Application No. PCT/US2014/031391 dated Jun. 24, 2014, 3 pages.

Primary Examiner — Cris L Rodriguez
Assistant Examiner — Hao D Mai (57) ABSTRACT

A plunger assembly for a cartridge for dispensing dental material. The plunger assembly has a receptacle, an activator, and a passageway extending through the receptacle along a longitudinal axis. The passageway forms a chamber for storing at least a component of the dental material and has an outlet for the chamber. The activator has a piston for extruding the component from the chamber and a plug for the outlet. The activator is movable to unplug the outlet and to subsequently extrude the component in a single stroke. The plunger assembly helps for reliably emptying the chamber and helps facilitating dispensation of dental materials.

6 Claims, 7 Drawing Sheets

(51) Int. Cl.
*A61C 5/66* (2017.01)
*A61C 5/68* (2017.01)

(56) References Cited

U.S. PATENT DOCUMENTS

| | | | | |
|---|---|---|---|---|
| 3,490,437 | A * | 1/1970 | Osten | A61J 1/2089 |
| | | | | 128/898 |
| 3,595,439 | A * | 7/1971 | Newby | A61C 5/064 |
| | | | | 206/219 |
| 3,684,136 | A * | 8/1972 | Baumann | A61C 5/064 |
| | | | | 206/219 |
| 3,756,390 | A * | 9/1973 | Abbey | A61M 5/284 |
| | | | | 206/219 |
| 4,449,645 | A * | 5/1984 | Korwin | B05C 17/00593 |
| | | | | 222/136 |
| 4,648,532 | A * | 3/1987 | Green | A61C 5/064 |
| | | | | 206/222 |
| 4,858,759 | A * | 8/1989 | Mauthe | B01F 13/002 |
| | | | | 206/219 |
| 4,941,751 | A * | 7/1990 | Muhlbauer | A61C 5/064 |
| | | | | 206/217 |
| RE33,801 | E | 1/1992 | Green | |
| 5,172,807 | A * | 12/1992 | Dragan | A61C 5/066 |
| | | | | 206/219 |
| 5,392,904 | A * | 2/1995 | Frick | A61C 5/064 |
| | | | | 206/219 |
| 6,319,002 | B1 * | 11/2001 | Pond | A61C 5/062 |
| | | | | 433/89 |
| 6,328,715 | B1 * | 12/2001 | Dragan | A21D 13/0025 |
| | | | | 604/232 |
| 6,379,152 | B1 * | 4/2002 | Dragan | A61C 5/066 |
| | | | | 433/90 |
| 6,386,872 | B1 * | 5/2002 | Mukasa | A61C 5/066 |
| | | | | 206/219 |
| 6,612,465 | B2 * | 9/2003 | Pierson | A61C 5/062 |
| | | | | 222/137 |
| 6,929,475 | B1 * | 8/2005 | Dragan | A61C 5/06 |
| | | | | 401/119 |
| 7,882,983 | B2 * | 2/2011 | Reidt | A61C 5/064 |
| | | | | 222/137 |
| 8,074,794 | B2 * | 12/2011 | Nakatsuka | B65D 81/3211 |
| | | | | 206/219 |
| 8,100,294 | B2 * | 1/2012 | May | B65D 47/2031 |
| | | | | 206/219 |
| 8,584,838 | B2 * | 11/2013 | Cheetham | A61C 5/064 |
| | | | | 206/219 |
| 8,893,925 | B2 * | 11/2014 | Cheetham | A61C 5/066 |
| | | | | 222/145.5 |
| 8,968,000 | B2 * | 3/2015 | Leiner | A61C 5/064 |
| | | | | 433/87 |
| 9,326,829 | B2 * | 5/2016 | Kojima | A61C 5/062 |
| 2001/0053511 | A1 * | 12/2001 | Aoyagi | A61C 5/062 |
| | | | | 433/90 |
| 2009/0152300 | A1 | 6/2009 | Hayman | |
| 2011/0017777 | A1 * | 1/2011 | Nakatsuka | B65D 81/3211 |
| | | | | 222/145.5 |
| 2011/0027751 | A1 * | 2/2011 | Kojima | A61C 5/064 |
| | | | | 433/90 |
| 2012/0258418 | A1 * | 10/2012 | Shen | A61C 19/066 |
| | | | | 433/29 |
| 2016/0045283 | A1 * | 2/2016 | Boehm | A61C 5/062 |
| | | | | 433/90 |

FOREIGN PATENT DOCUMENTS

| | | |
|---|---|---|
| WO | WO 2000-45732 | 8/2000 |
| WO | WO 2003-028871 | 4/2003 |
| WO | WO 2005-094714 | 10/2005 |
| WO | WO 2011-029131 | 3/2011 |

* cited by examiner

PLUNGER ASSEMBLY AND A CAPSULE FOR DISPENSING A DENTAL MATERIAL

FIELD OF THE INVENTION

The invention relates to a plunger assembly having a receptacle and an activator. In particular the invention relates to a plunger assembly which has a receptacle with a chamber for containing at least a component of dental material and a chamber outlet, and the activator forming a piston for extruding the component from the chamber and additionally forming a plug for openably closing the outlet.

BACKGROUND

Dental substances are often provided in devices allowing the substance to be dispensed directly to a desired location, for example on a dental pad or in a patient's mouth. Such dispensing devices typically have a chamber for holding the dental substance, an outlet, and a piston for extruding the substance from the chamber through the outlet.

A variety of dispensing devices are designed for dispensation of relatively high viscosity dental substances, like for example dental filling materials. Some of those dispensing devices are configured for use with an applicator providing an extrusion force that is sufficient for dispensation of high viscosity dental substances. In dentistry several types of manually operated applicators are available which provide leverage for increasing manual forces to provide sufficient extrusion forces. Many applicators are designed as a reusable tool which forms part of a dental practice's basic equipment.

Although a variety of applicators and dispensing devices are available there is a desire to provide a dispensing device which can be used with applicators already available in the market. Further it is desirable to provide a dispensing device which is easy to use in combination with such applicators, and which is further relatively inexpensive.

SUMMARY OF THE INVENTION

The invention is directed to a plunger assembly. Such plunger assembly may be used alone for dispensing at least a component of a dental material or in combination with a cartridge for dispensing a dental material. The plunger assembly comprises a receptacle and an activator. A passageway extends through the receptacle along a longitudinal axis. The a longitudinal axis may be linear or curved (in particular circular). The passageway extends over a first section along the longitudinal axis at a first inner cross-section, and extends over a second section along the longitudinal axis at a greater second inner cross-section. For example the passageway may extend over the first section at a first inner diameter, and over the second section at a greater second inner diameter.

At least part of the second section of the passageway forms a chamber for storing at least a component of the dental material. Further the first section of the passageway forms an outlet for the chamber.

The activator is movably received within the passageway for a movement along the longitudinal axis. The activator has a first portion, a second portion and a third portion each extending along the longitudinal axis. The third portion is arranged between the first and second portion. The first portion forms a plug for the outlet, in particular for sealing the outlet. The first portion accordingly has a first outer cross-section which is adapted for sealing with the first inner cross-section of the receptacle. In particular the first portion accordingly may have a first outer diameter which may be adapted for sealing with the first inner diameter of the receptacle.

The second portion of the activator forms a piston for extruding the component (or dental material) from the chamber. The second portion has a second outer cross-section which is adapted for sealing with the second inner cross-section of the receptacle. In particular the second portion may have a second outer cross-section which may be adapted for sealing with the second inner cross-section of the receptacle.

The third portion of the activator has a third outer cross-section that is smaller than the first inner cross-section. Further preferably the third outer cross-section is smaller than the second inner cross-section. In particular the third portion of the activator may have a third outer diameter that is smaller than the first inner diameter and preferably the third outer diameter may also be smaller than the second inner diameter.

The invention is advantageous in that it provides a plunger assembly which may be reliably activated. In particular the invention provides for a relatively constant activation force of the plunger assembly. Further activation of the plunger assembly preferably does not require rupturing or breaking any parts, and therefore helps avoiding undesired particles in the material dispensed and undesired high activation forces due to tolerances in manufacturing of predetermined breaking areas. The invention is further advantageous in that the plunger assembly may be manufactured at minimized costs, because the plunger assembly basically may comprise only two parts.

In one embodiment the activator is movable within the receptacle between an inactivated position, in which the plug seals the outlet, and an activated position, in which an opening for the chamber is formed between the third portion of the activator and the outlet. In the activated position the plug is preferably located outside the receptacle and the piston is at least partially, more preferably entirely, received within the receptacle.

In a further embodiment the receptacle has a least two outlets. In this embodiment the activator has a first pin formed by the first and third portion and at least a second pin. The second pin functionally corresponds in configuration to the first pin such that the activator forms at least two plugs for sealing the outlets. In particular the first and second pins may have the same shape and size, or at a similar shape and different sizes.

In one embodiment the first and second portion of the activator are disconnected. In particular the first and second portion of the activator may be disconnectably engaged with each other. In other embodiments however the activator including the first second and third portion (and optionally one or more additional pins) may be formed in a single piece, for example monolithically.

In one embodiment the first section of the passageway of the receptacle and the second section of the passageway of the receptacle are arranged coaxially with the longitudinally axis. Further the first, second and third portion of the activator are preferably arranged coaxially with the longitudinally axis.

In an alternative embodiment the first section of the passageway of the receptacle and the second section of the passageway of the receptacle are arranged in an off-center relationship to the longitudinally axis, and wherein the first, second and third portion of the activator are arranged in a corresponding off-center relationship to the longitudinally axis.

In one embodiment the plunger assembly has a retainer for retaining the plunger assembly in a dispensing gun. Thus the plunger assembly may itself form a capsule for dispensing the dental material. In a further embodiment the plunger assembly has a cannula which forms a channel between a free dispensing end of the cannula and the outlet of the receptacle. The channel of the cannula at least adjacent the outlet has a widened portion being larger in cross-section than the outlet. The widened portion may be ball or disk shaped. Further the plunger assembly may be adapted such that at least part of the first and third portion of the activator are bent by a wall of the widened portion in the activated position.

In a further aspect the invention concerns a capsule for storing and dispensing a dental material. The capsule comprises a compartment and further comprises a plunger assembly of the invention. The plunger assembly is preferably received within the compartment. The plunger assembly further may have an outer sealing structure for sealing with an inner wall that forms at least part of the compartment.

In a further embodiment the capsule comprises a first powdery component of the dental material within the compartment and outside the plunger assembly, and a second liquid component of the dental material within the chamber of the plunger assembly. In one embodiment the capsule further comprises a retainer for retaining the plunger assembly in a dispensing gun.

In a further embodiment the capsule has a capsule outlet for dispensing the dental material from the compartment, and a dispensing nozzle for guiding the dental material from the capsule outlet toward a free dispensing end of the nozzle. In a further embodiment the capsule is configured such that the plunger assembly is movable within the capsule compartment such that the dental material can be substantially entirely extruded from the compartment.

BRIEF DESCRIPTION OF THE FIGURES

FIG. 5A-1 is a front view of a receptacle front wall with outlets configured to correspond to the pins in the plunger assembly of FIGS. 5A-5B;

DETAILED DESCRIPTION OF THE INVENTION

Figure 1:
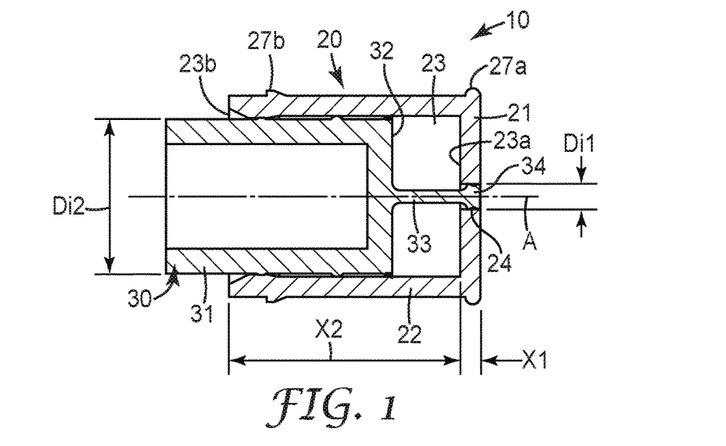
FIG. 1 is a cross-sectional view of a plunger assembly according to an embodiment of the invention in an inactivated position.

FIG. 1 shows an example of a plunger assembly 10 according to the invention. The plunger assembly comprises a receptacle 20 and an activator 30. The receptacle 20 is generally cup-shaped. In particular the cup shape is provided by a generally planar disc-shaped receptacle front wall 21, and a generally cylindrical and circumferential side wall 22 extending or protruding along a longitudinal axis A from one side of the receptacle front 21. The side wall 22 and the front wall 21 in combination form a generally cylindrical chamber 23 within the receptacle 20. The receptacle 20 thus is adapted such that at least a, preferably liquid, component of a dental material can be received within the chamber 23. The chamber 23 at a first or front end 23a is delimited by the receptacle front wall 21, is open at its opposite second or rear end 23b, and extends generally cylindrical between the chamber front end 23a and rear end 23b. Further the receptacle front wall 21 comprises a through-hole which extends between opposite wall surfaces of the receptacle front wall 21. The through-hole forms an outlet 24 for the chamber 23. In the example the outlet 24 extends generally cylindrical and parallel to, in particular coaxial with, the longitudinal axis A. Therefore the chamber 23 and the outlet 24 together form a passageway extending along the longitudinal axis A through the receptacle 20. The so formed passageway extends over a first section X1 (in an area of the chamber 23) along the longitudinal axis A at a first inner cross-section with a first inner diameter Di1, and over a second section X2 (in an area of the outlet 24) along the longitudinal axis extends at a wider second inner cross-section with a second inner diameter Di2. Accordingly the passageway through the receptacle has a stepped configuration. The receptacle further has at least one annular seal, for example an annular front seal 27a and an annular real seal 27b, for sealing with a cartridge for dispensing dental material.

In the example the receptacle 20 and the activator 30 are telescopically assembled, such that the activator 30 is movably received within the passageway for a movement along the longitudinal axis A. In particular the activator 30 has a piston 31 which extends generally cylindrical along the longitudinal axis A. The piston 31 further is adapted for sealingly sliding within the chamber 23 of the receptacle 20. The piston 31 has a front face 32 which generally corresponds in shape to the inner surface of the receptacle front wall 21, and which in the example shown is generally planar. Accordingly the front face 32 of the piston 31 matches in shape with the side of the receptacle front wall 21 facing the piston 31. Therefore the piston 31 is adapted to displace generally the entire amount of a component received in the chamber 23 in a position of the piston 31 at an end position (shown in FIG. 2) in which the piston front face 32 abuts the receptacle front wall 21. The activator 30 further has a pin 33 which protrudes from the front face 32 of the piston 31. The pin 33 extends generally parallel to the longitudinal axis A and in this example extends generally coaxial with the longitudinal axis A. The pin 33 forms (over a partial section of its length) a first portion of the activator 30 which is also further referred to as plug 34. The plug 34 is shaped and sized such that it can seal the receptacle outlet 24. The plug 34 of the activator 30 in particular has a first outer cross-section which preferably is slightly oversized relative to the first inner cross-section of the outlet 24 of the receptacle 20. In particular the plug 34 has a first outer cross-section with a first outer diameter Do1 which is equal or greater than the inner diameter Di1 so as to provide a seal between the plug 34 and the outlet 24. Further the piston 31 forms a second portion of the activator 30. The piston 31 has a second outer cross-section which is adapted for sealing with the chamber 23 of the receptacle 20 (or with the second inner cross-section of the passageway). Such second outer cross-section in the example has a second outer diameter Do2 which preferably is equal or greater than the second inner diameter Di2 so as to provide a seal between the piston 31 and the side wall 22 of the chamber 23. Further in the example the second outer cross-section and/or the second outer diameter Do2 are greater than the first outer cross-section and/or the first outer diameter Do1, respectively. Thus the chamber volume may be maximized.

In an inactivated position as shown in FIG. 1 the activator 30 is positioned such that the plug 34 is located within the receptacle outlet 24. Accordingly the piston 31 and the plug 34 in the inactivated position seal the chamber 23 substantially hermetically, and thus can encapsulate at least a component of a dental material.

Figure 2:
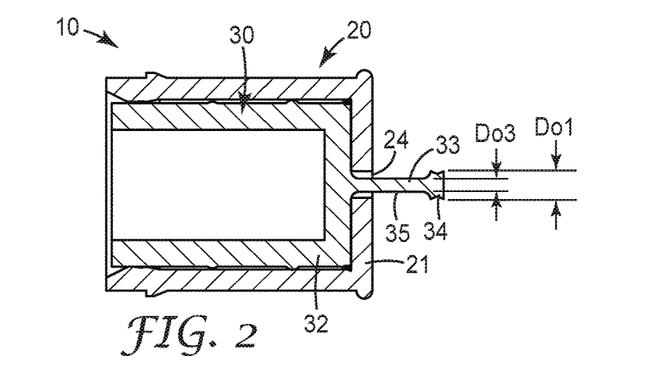
FIG. 2 is a cross-sectional view of the plunger assembly shown in FIG. 1 in an activated position.

FIG. 2 shows the plunger assembly 10 in an activated position, in which substantially all of the chamber contents is extruded from the chamber. The travel from the inactivated position to the activated position further comprises an initial activation stroke in which the plug 34 still seals or plugs the outlet 24, and a main activation stroke in which the plug 34 is located outside the outlet 24 with the pin 33 reaching through the outlet 24 toward the piston 31. The pin 33 between the first portion (or plug 34) of the activator 30 and the second portion (or piston 31) of the activator forms a third portion (also further referred to as connector 35). The connector has a third outer cross-section that is smaller than the first inner cross-section of the receptacle. In the example the connector 35 has a third outer cross-section with a third outer diameter Do3 which is smaller than the first outer diameter Do1 and which is also smaller than the second outer diameter Do2. Further the third outer diameter Do3 is smaller than the first inner diameter Di1 of the receptacle 20 and is also smaller than the second inner diameter Di2 of the receptacle 20. Thus the connector 35 does not entirely fill outlet 24 when positioned therein so that a channel is left, through which the chamber contents can flow during the main activation stroke.

As described above during movement over the initial activation stroke the plug 34 seals the outlet 24. Further due to the different cross-sections (or diameters) of the piston 31 and the plug 34, the volume displaced by the piston 31 in the chamber is greater than the volume successively freed by the plug 34 in the outlet 24. Accordingly the volume formed between the activator 30 and the receptacle 20 decreases during the initial activation stroke. Therefore during the initial activation stroke a pressure generated within the volume in response to the movement also counteracts such movement. Thus during the initial activation stroke an initial activation force is created which preferably rapidly decreases upon the initial activation stroke transitioning into the main activation stroke. For example if the chamber 23 is filled with an incompressible liquid typically a higher initial activation force is required to unplug the outlet 24 and a lower subsequent activation force is sufficient to extrude the liquid from the chamber 23. The rapid decrease of the force preferably also causes a rapid and therefore substantially complete emptying of the chamber during manual activation. This is because a user exerting a relative high activation force naturally does not react fast enough to reduce the force before the chamber is empty. It has been found that the initial activation force can be adjusted substantially constant for a plurality of piston assemblies which is advantageous in comparison to piston assemblies of the prior art based on rupturing of seals.

It has been further found that the volume decrease during unplugging is typically compensated via resilience of the receptacle and/or the piston as well as by a certain amount of air or gas being naturally present in the chamber after filling. The person skilled in the art will however recognize possibilities to control such volume compensation by design of the plunger assembly and/or by filling with a composition from a liquid including air or gas. Such initial activation force during initial activation further helps avoiding unintentional activation, for example during transport of the plunger assembly.

Figure 3:
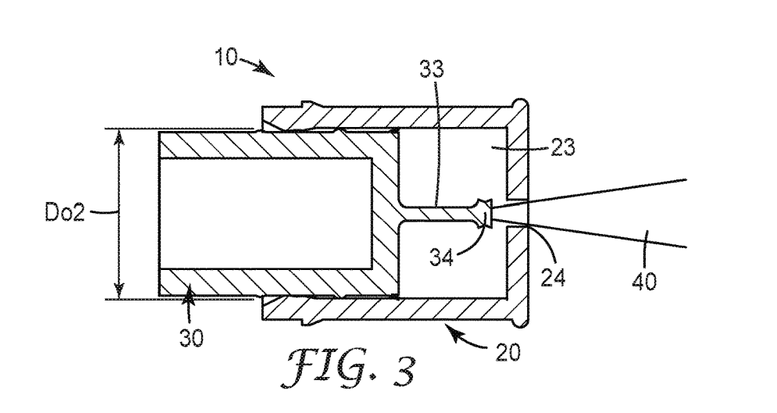
FIG. 3 is a cross-sectional view of the plunger assembly shown in FIG. 1 in a filling position.

FIG. 3 illustrates the plunger assembly 10 in a filling position, in which the chamber 23 can be filled, for example with a liquid. In the filling position the activator 30 is positioned relative to the receptacle 20 such that the pin 33 is entirely located outside the outlet 24. A filling needle 40 may be placed in the outlet 24 and used to guide the liquid in the chamber 23. The receptacle 20 may be at least in an area adjacent the outlet 24 made of a resilient material, for example a rubber or thermoplastic elastomer, whereas other portions of the receptacle may be made of plastic materials like polyethylene, polypropylene or another appropriate polymer which is less resilient than the rubber or thermoplastic elastomer used adjacent the outlet 24. Alternatively each of the activator 30 and the receptacle 20 may be made of one uniform material and a resilient zone around the outlet 24 may be provided by design, for example by a reduced wall thickness.

During filling the filling needle 40 (which may be oversized relative to the outlet 24) may resiliently widen the outlet 24. Accordingly the plug 34, although normally being adapted to seal the outlet 24, may not be capable of sealing the widened outlet. Hence after filling and for positioning the plunger assembly from the filling position (FIG. 3) to the inactivated position (FIG. 1) excess material and/or air within the chamber may be released through a gap between the plug 34 and the widened outlet 24. Thereby the filling needle 40 may be successively retracted from the outlet 24 as the activator 30 is moved toward the inactivated position. The filling needle 40 may at that stage further used to suck excess material and/or air back from the plunger assembly 10.

Figure 4A:
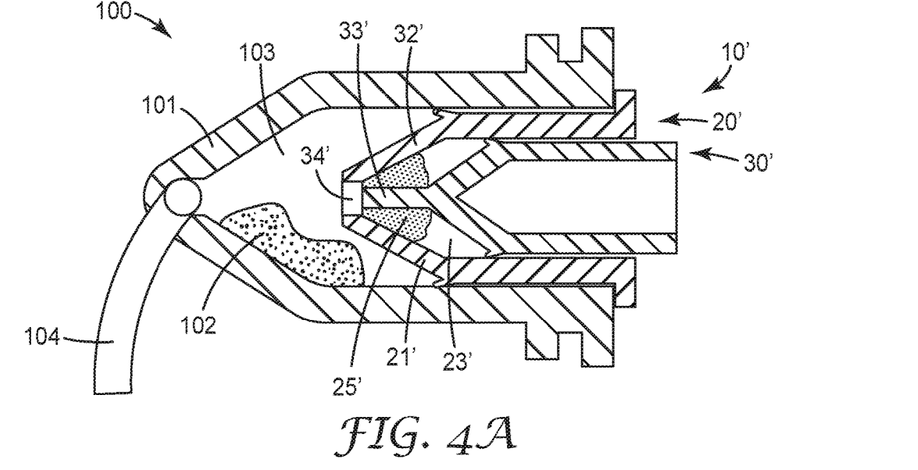
FIGS. 4A-4B are cross-sectional views of a capsule comprising a plunger assembly according to an embodiment of the invention.
Figure 4B:
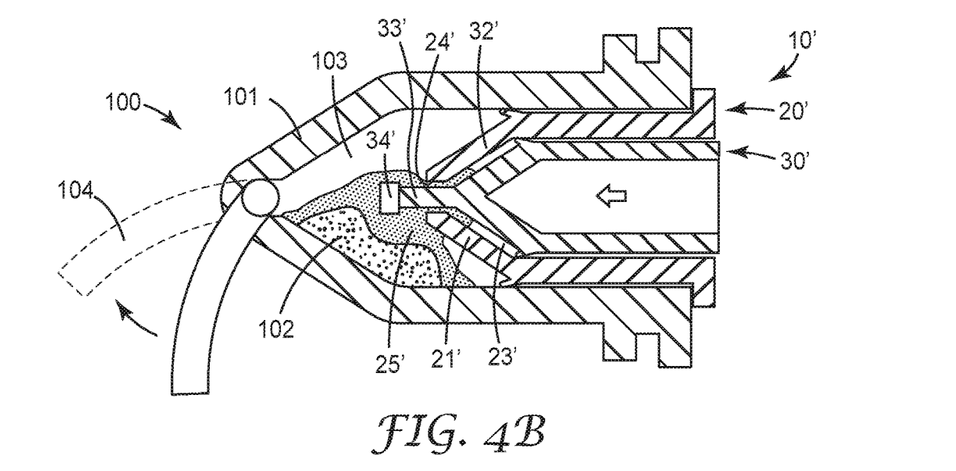

FIG. 4A and FIG. 4B show a capsule 100 comprising a plunger assembly 10' which is substantially identical with the plunger assembly 10 shown in FIGS. 1 to 3. The only difference between the plunger assembly 10' and the plunger assembly 10 is the shape of the piston front face 32' and the receptacle front wall 21' of the receptacle 20'. In this example piston front face 32' of the activator 30' and the side of the receptacle front wall 21' facing the front wall 21' are conically shaped. In particular the piston front face 32' tapers in a direction toward the receptacle front wall 21' and the receptacle front wall 21' has a corresponding matching shape. It has been found that such a shape helps reliably emptying the chamber 23' upon activating the plunger assembly 10'. The activator 30' further includes a pin 33' and a plug 34' configured to seal an outlet 24' of the receptacle 20'.

The capsule 100 has a cartridge 101 forming a capsule chamber 103 which in the example is partially filled with a powder 102. Further a liquid 25' is contained within chamber 23' of the plunger assembly 10'. The powder 102 and the liquid 25' are preferably adapted to form a hardenable dental material when the powder 102 and the liquid 25' are mixed with one another. In the inactivated position of the plunger assembly 10' the powder and the liquid 25' are stored within the capsule 100 separate from each other, in particular in a non-contact relationship to each other. Thus, the powder and liquid may be stored in the capsule over a relatively long time period and mixed together only shortly before use.

The capsule 100 further has a nozzle 104 which forms a capsule outlet for dispensing the dental material mixed from the powder 102 and liquid 25'. For mixing the powder 102 and the liquid 25' the plunger assembly 10' can be activated by moving the activator 30' and the receptacle 20' in the activated position (shown in FIG. 4B). The capsule 100 is preferably adapted such that the capsule chamber 103 has a greater volume than the volume of the joint amount of powder and liquid contained in the capsule when mixed. Accordingly, the capsule 100 is adapted such that the liquid 25' can be extruded from the plunger assembly 10' into the capsule chamber 103. The powder 102 and the liquid 25', once joined in the capsule chamber 103, can be mixed by triturating, for example in a dental capsule shaker. The nozzle 104 is preferably pivotable between a closed position, in which the capsule outlet is closed, and an open position, in which the capsule outlet is open (FIG. 4B). For mixing the powder 102 and the liquid 25', the nozzle 104 is preferably positioned to the closed position. Thus, the capsule chamber 103 is entirely closed by the nozzle 104, on the one hand, and the plunger assembly 10', on the other hand. Therefore, any component or dental material may be prevented from being urged out of the capsule during mixing. For dispensing the mixed material the plunger assembly (still in the activated position) may be moved within the capsule chamber 103 toward the nozzle 104 so that mixed dental material is displaced from the capsule chamber and dispensed through the capsule outlet of the nozzle 104. Therefore the plunger assembly 10' also forms a piston for dispensing the dental material from the capsule 100. The capsule cartridge 101 is preferably shaped such that the chamber walls generally conform in shape to the plunger assembly 10' without substantially leaving spaces between the plunger assembly 10' and the capsule cartridge 101 in an end position (not shown) of the plunger assembly 10' in the capsule cartridge 101. The end position of the plunger assembly 10' in the capsule cartridge 101 is a position in which the receptacle front wall 21' touches or substantially touches the corresponding chamber wall of the capsule 100 and in which substantially all of the dental material is displaced out of the capsule chamber 103. The cartridge 101 is further preferably shaped such that it can accommodate pin 33' and plug 34' (protruding from the plunger assembly 10' in the activated position) in the end position of the plunger assembly 10' within the capsule 100.

Figure 5A:
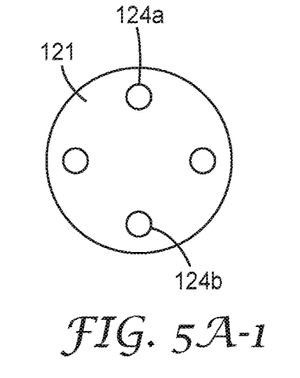
Figure 5A:
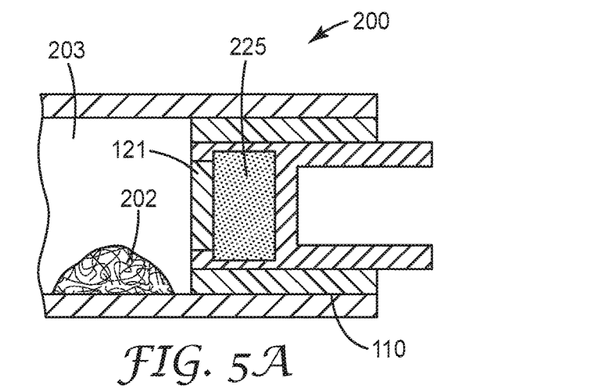
FIGS. 5A-5B illustrate cross-sectional views of a capsule comprising a further plunger assembly according to an embodiment of the invention.
Figure 5B:
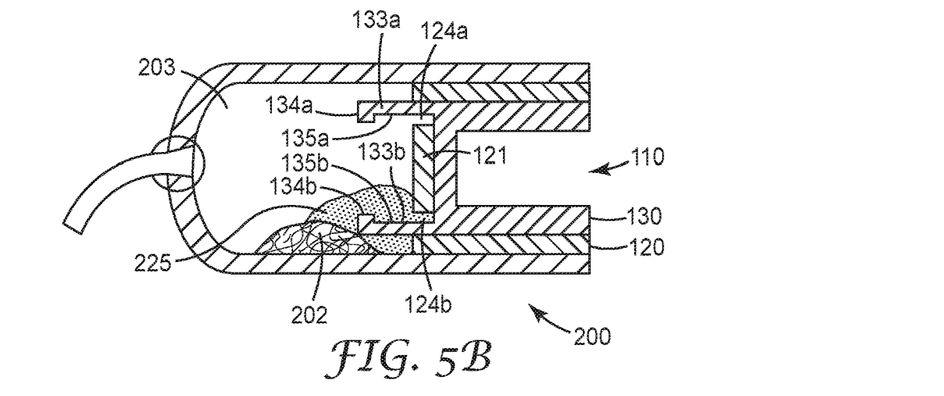

FIGS. 5A, 5A-1, and 5B show a capsule 200 which is identical to the capsule 100 shown in FIGS. 4A-4B but comprises an alternative plunger assembly 110. Further the plunger assembly 110 corresponds to the plunger assembly 10 (shown in FIGS. 1 to 3) except that the plunger assembly 110 has an activator 130 that comprises at least two pins 133a, 133b (in the example four pins) and a receptacle 120 that comprises a front wall 121 with corresponding at least two outlets 124a, 124b (in the example four outlets, as shown in FIG. 5A-1). Each of the pins 133a, 133b is identically configured as the pin 33 shown in FIGS. 1 to 3. In particular each of the pins 133a/133b has a plug 134a/134b, respectively, for sealing the respective outlet 124a/124b in the front wall 121. Further each of the pins 133a/133b has a connector 135a/135b which is reduced in cross-section and/or diameter relative to the plug 134a/134b. Accordingly the basic function of the plunger assembly 110 corresponds to the function of the plunger assembly 10 of FIGS. 1 to 3. However, plunger assembly 110 preferably provides for pre-distributing the liquid 225 extruded from the plunger assembly 110 into the capsule chamber 203. Thus the homogeneity of a mixture of a powder 202 and the liquid 225 within the capsule 200 may be maximized.

Figure 6:
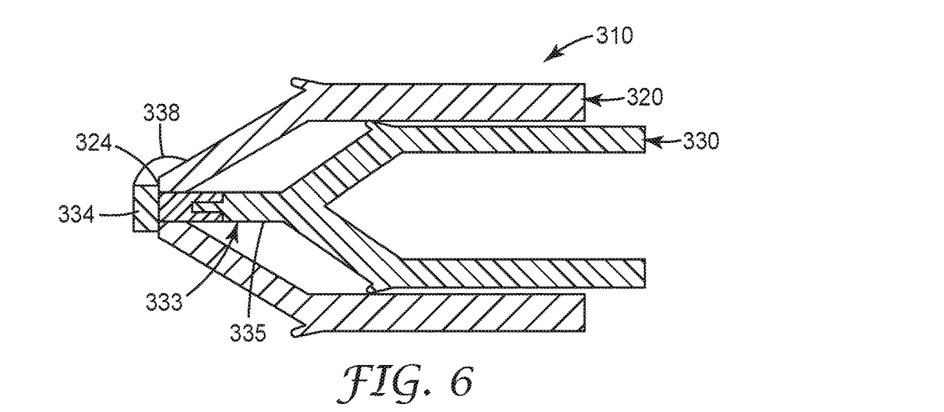
FIG. 6 is a cross-sectional view of a plunger assembly according to an embodiment of the invention.

FIG. 6 shows a plunger assembly 310 which corresponds to the plunger assembly 10 (shown in FIGS. 1 to 3) except that the plunger assembly 310 has an activator 330 in which the pin 333 is made of two separable pieces. The pin 333 of this example has a plug portion 334 and a connector portion 335 which are disconnectably engaged with each other, for example by a plug/socket connection. The plunger assembly 310 is adapted such that the connector portion 335 can push the plug portion 334 out of outlet 324 for activation of the plunger assembly 310. Once the transition area between the plug portion 334 and the connector portion 335 is positioned outside the outlet 324 the plug portion 334 may separate from the connector portion 335. Accordingly, the pin 333 may automatically reduce in length. As a consequence, in use of the plunger assembly 310 in a capsule, any adverse effects in mixing and extrusion of the dental material (not shown in FIG. 6) as they may be caused by a long pin 333 protruding in the capsule chamber may be minimized. The plug portion 334 may be secured to the receptacle 320 by a holding strap 338. This helps preventing the plug portion 334 to get intermingled into the mixed dental material and to avoid that the plug portion 334 blocks of the capsule outlet during dispensation of the dental material.

Figure 7:
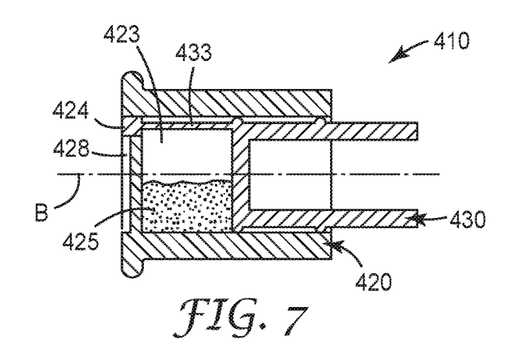
FIG. 7 is a cross-sectional view of a further plunger assembly according to an embodiment of the invention.
Figure 7A:
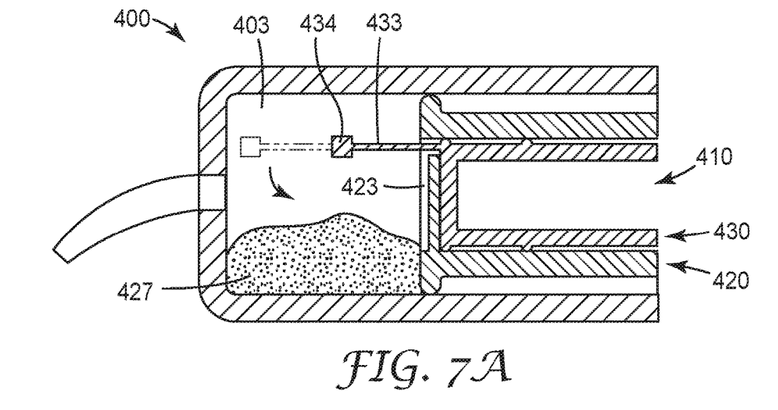
FIGS. 7A-7B are cross-sectional views of a capsule comprising the plunger assembly of FIG. 7.
Figure 7B:
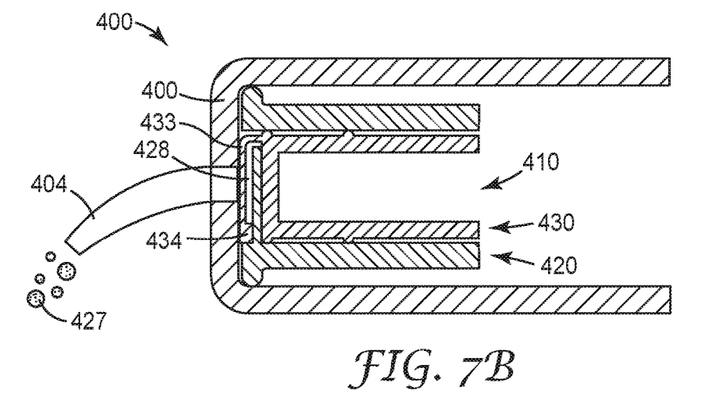

FIG. 7 shows a plunger assembly 410 which corresponds to the plunger assembly 10 (shown in FIGS. 1 to 3) except that the plunger assembly 410 has an activator 430 in which the pin 433 is arranged in an off-center relationship relative to the longitudinal axis B, and a receptacle 420 which has a correspondingly arranged outlet 424 and a recess 428 in the receptacle front face for accommodating the pin 433 when bent. The pin 433 may be bent during use of the plunger assembly 410 for dispensing a liquid dental material 425 from a chamber 423 into a chamber 403 of a capsule 400 (FIG. 7A) to mix with a powdered dental material in the chamber 403 to form a mixed powder and liquid dental material 427. In this case the pin 433 may protrude from the activated plunger assembly (shown in FIG. 7A) and urging the plunger assembly 410 toward an end position within the capsule chamber 403 (shown in FIG. 7B) the pin 433 may be bent by the capsule wall 401 in a direction laterally to the longitudinal axis B and received in the recess 428 (FIG. 7B). Thus, any adverse effects during extrusion of the dental material 427, for example unintentional plugging of the capsule outlet 404 by the pin 433, may be minimized. Further this helps minimizing any residual dental material 427 in the emptied capsule.

Figure 8:
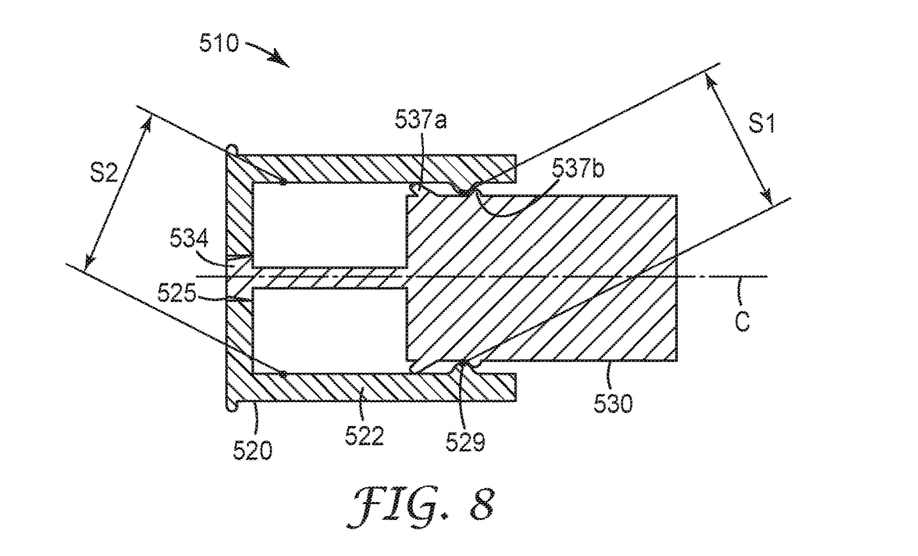
FIG. 8 is a cross-sectional view of a plunger assembly according to an embodiment of the invention.

FIG. 8 shows a further embodiment of a plunger assembly 510 which may also be used in combination with the embodiments shown in FIGS. 1 to 7. The receptacle 520 in the example has a side wall 522 with an inner, preferably annular, bulge 529. Further the activator 530 has an annular front seal 537a and an annular rear seal 537b which are spaced from each other in a dimension along the longitudinal axis C. The inner bulge 529 has a diameter S1 which is smaller than an outer diameter of the annular rear seal 537b of the activator. Further the annular rear seal 537b may have an equal or smaller diameter than the annular front seal 537a of the activator 510. The annular front seal 537a has—at least when received within the receptacle 520—a diameter S2 which is larger than the diameter S1. In the inactivated position of the plunger assembly 510 the activator 530 and the receptacle 520 are positioned relative to each other such that the receptacle bulge 529 is located between the front and rear seal 537a, 537b of the activator 530. Accordingly the activator 530 and the receptacle 520 are retained via the bulge 529 and seals 537a/537b against a movement relative to each other. Further for a movement of the activator 530 and the receptacle 520 relative to each other toward the activated position an increased initial activation force is provided by the bulge 529 and rear seal 537b relative to embodiment without such bulge and seal. Therefore once the increased initial activation force is overcome the rear seal 537b preferably moved past the bulge 529 with the consequence that the force for any further movement drops rapidly. In addition the plunger assembly 510 is preferably adapted such that on a travel from the inactivated position toward the activated position at a position in which the rear seal 537b has passed the bulge 529 the plug 534 is located outside the outlet 524. Accordingly at that stage the initial activation stroke transitions into the main activation stroke in which the force required for any further movement is relatively low in comparison to the initial activation force.

Figure 9:
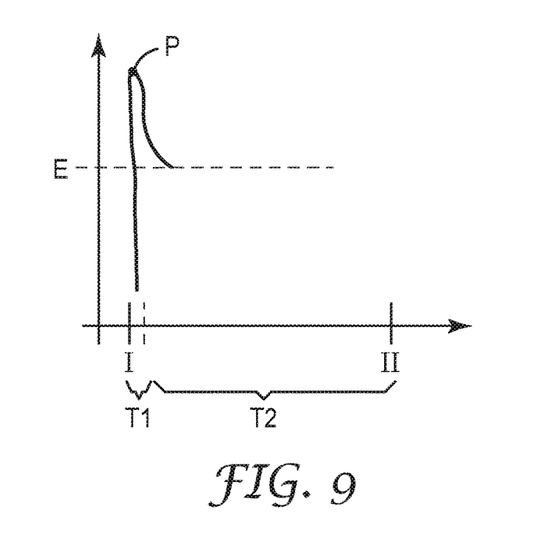
FIG. 9 is a diagram showing a force curve for activation of a plunger assembly according to an embodiment of the invention.

FIG. 9 qualitatively illustrates a curve representing the required force for a movement of the activator 530 and the receptacle 520 relative to each other on a travel from the inactivated position I to the activated position II. The initial activation force during the initial activation stroke T1 has a peak (and ends) at point P and rapidly drops toward an extrusion force E within the main activation force T2. An embodiment having a bulge and seal as illustrated in FIG. 8 typically has a higher peak force P than an embodiment without such bulge and seal, although in the latter embodiment a higher initial activation force and a lower extrusion force is also provided.

Figures 10A, 10B:
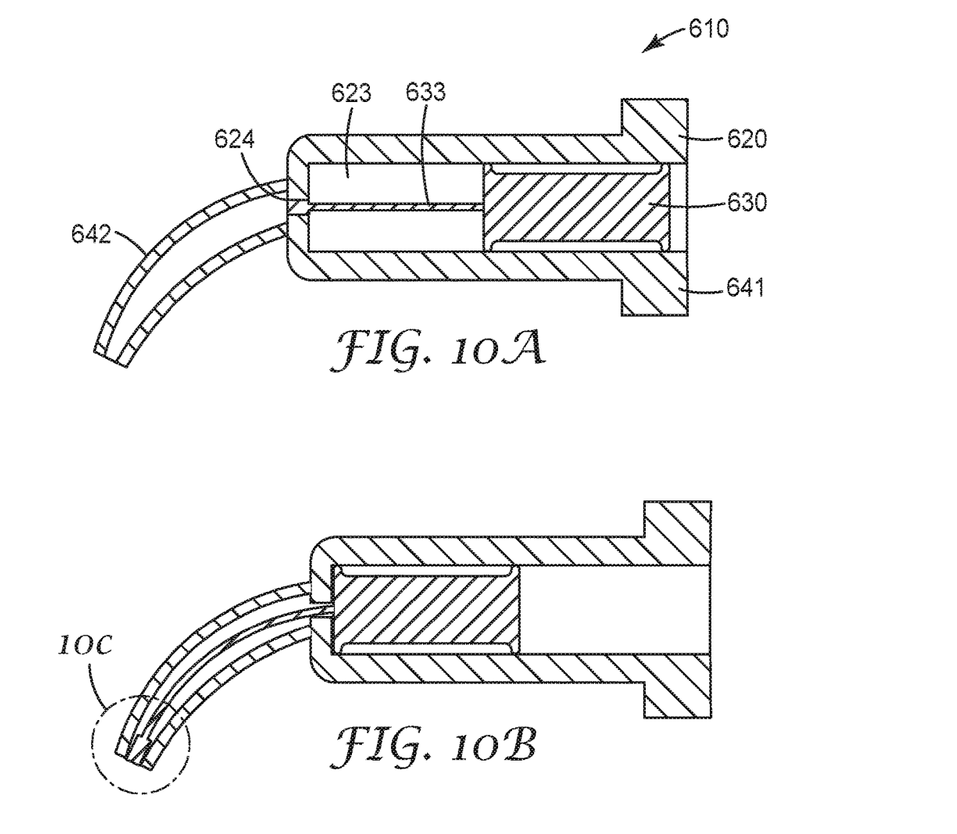
FIGS. 10A-10C are cross-sectional views of a plunger assembly according to an embodiment of the invention.
Figure 10C:
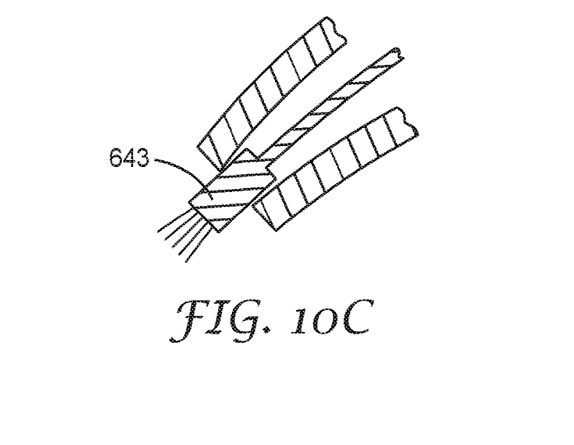

FIG. 10A to FIG. 10C show a further plunger assembly 610 which as such is configured as a capsule for dispensing a dental material. The plunger assembly 610 has a receptacle 620 and an activator 630. The configuration of the plunger assembly 610 corresponds to the configuration of the example shown in FIGS. 1 to 3, but differs in that the plunger assembly 610 additionally has a retainer 641, a nozzle 642 and an optional applicator brush 643. The retainer 641 allows the plunger assembly 610 to be retained in a dispensing gun for urging the activator 630 forward at relatively high forces. Further, the receptacle 620 has an outlet 624 which opens into the nozzle 642. Accordingly, in a movement of the activator 630 and the receptacle from the inactivated position (FIG. 10A) toward the activated position a material contained in chamber 623 is guided through the nozzle 642. Thereby the pin 633 also moves into the nozzle 642. The pin 633 and the nozzle 642 are therefore sized such that material can flow through a gap between the pin 633 and the nozzle 642 when the pin 633 is located in the nozzle. In one example, the pin 633 is dimensioned such that it protrudes outside the free end of the nozzle 642 at least in the activated position (FIG. 10B) of the plunger assembly 610. In this example the pin 633 may additionally serve as an applicator element. Further, in one particular example, such applicator element is an applicator brush 643 (shown in FIG. 10C). The applicator brush 643 may be used to pick up a portion of material dispensed from the plunger assembly 643 and for applying a portion of that material to a desired place.

Figure 11A:
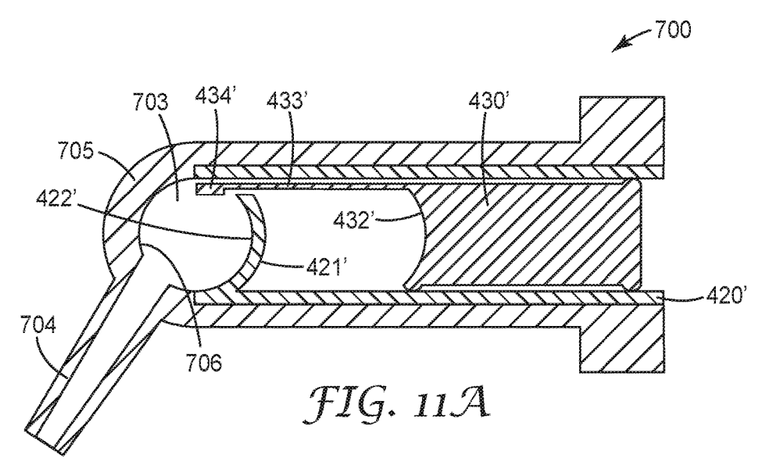
FIGS. 11A-11B are cross-sectional views of a capsule comprising a further plunger assembly according to an embodiment of the invention.
Figure 11B:
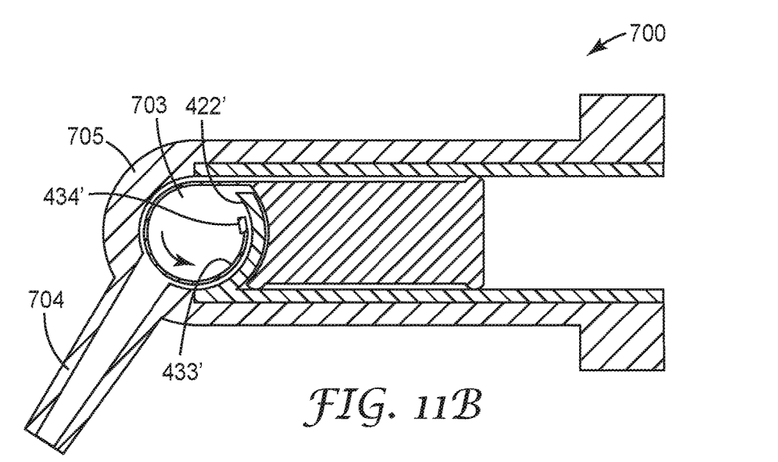

FIG. 11A and FIG. 11B show a capsule 700 having a plunger assembly 410' which corresponds to the plunger assembly 410 shown in FIG. 7 except that the receptacle 420' has a concave ball-shape or concave cylindrically shaped front wall 421' and the activator 430' has a front face 432' which matches the shape of the side of that that front wall 421' which the front face 432' faces to. The capsule 700 has a capsule chamber 703 having a concave ball-shape or concave cylindrically shaped inner side wall 706 of a capsule front wall 705. The inner side wall 706 of the capsule front wall 705 in combination with the receptacle front wall 421' preferably form a hollow ball or hollow cylinder in the activated position of the plunger assembly 410', as shown in FIG. 11B. In the activated position of the plunger assembly 410' the pin 433' is bent generally circular by the inner side wall 706 of the capsule front wall 705 and eventually by an outer side wall 422' of the receptacle front wall 421'. A movement of the plunger assembly 410' further toward the capsule front wall 705 for extruding dental material from the capsule chamber 703 preferably causes the pin 433' to further coil in the space between the inner side wall 706 of the capsule front wall 705 and the outer side wall 422' of the receptacle front wall 421'. Thus the pin 433' is prevented to hinder in dispensing the dental material from the outlet 704.

The invention claimed is:

1. A plunger assembly for a cartridge for dispensing dental material, the plunger assembly comprising:
   a receptacle, an activator, and a passageway extending through the receptacle along a longitudinal axis;
   wherein the passageway over a first section along the longitudinal axis extends at a first inner cross-section, and over a second section along the longitudinal axis extends at a greater second inner cross-section;
   at least part of the second section forming a chamber for storing at least a component of the dental material and the first section forming an outlet for the chamber;
   the activator having a first portion, a second portion and a third portion extending along the longitudinal axis with the third portion being arranged between the first and second portion;
   the first portion forming a plug for the outlet and having a first outer cross-section adapted for sealing with the first inner cross-section, and
   the second portion forming a piston for extruding the component from the chamber and having a second outer cross-section adapted for sealing with the second inner cross-section to provide a seal between the piston and a side wall of the chamber;
   wherein the third portion has a third outer cross-section that is smaller than the first inner cross-section;
   wherein the activator is movably received within the passageway for a movement along the longitudinal axis between an inactivated position, in which the plug seals the outlet, and an activated position, in which the outlet comprises an opening formed between the third portion of the activator and the outlet;
   a cannula which forms a channel between a free dispensing end of the cannula and the outlet of the receptacle, and wherein the channel, at least adjacent the outlet, has a widened portion being larger in cross-section than the outlet; and wherein at least a part of the first and third portion of the activator are bent by a wall of the widened portion when the activator is in the activated position.

2. The plunger assembly of claim 1, wherein the first section of the passageway of the receptacle and the second section of the passageway of the receptacle are arranged coaxially with the longitudinal axis, and wherein the first, second and third portion of the activator are arranged coaxially with the longitudinal axis.

3. The plunger assembly of claim 1, wherein the first section of the passageway of the receptacle and the second section of the passageway of the receptacle are arranged in an off-center relationship to the longitudinal axis, and wherein the first, second and third portion of the activator are arranged in a corresponding off-center relationship to the longitudinal axis.

4. The plunger assembly of claim 1, wherein a surface of the receptacle further comprises a retainer for retaining the plunger assembly in a dispensing gun.

5. The plunger assembly of claim 1, wherein the widened portion is ball or disk shaped.

6. The plunger assembly of claim 1, wherein the first portion of the activator protrudes beyond a free end of the cannula when the activator is in an activated position, and wherein the first portion of the activator further comprises a brush.

* * * * *